United States Patent [19]

Higashide et al.

[11] Patent Number: 4,575,489
[45] Date of Patent: Mar. 11, 1986

[54] STREPTOMYCES ALBULUS SUBSP. OCHRAGERUS SUBSP. NOV. CULTURE FOR MAKING PEPTIDE

[75] Inventors: Eiji Higashide, Takarazuka; Satoshi Horii, Sakai, both of Japan

[73] Assignee: Takeda Chemical Industries, Ltd., Osaka, Japan

[21] Appl. No.: 300,285

[22] Filed: Sep. 8, 1981

[30] Foreign Application Priority Data

Sep. 18, 1980 [JP] Japan ................................ 55-130298

[51] Int. Cl.$^4$ .......................... C12P 21/02; C12N 1/20; C07D 207/00
[52] U.S. Cl. ...................................... 435/70; 435/121; 435/253; 435/887; 514/425; 548/530
[58] Field of Search .................. 435/68, 886, 887, 70, 435/71, 122, 253, 121; 260/326.48; 548/530

[56] References Cited

U.S. PATENT DOCUMENTS 4,355,112 10/1982 Okumura et al. ..................... 435/71

OTHER PUBLICATIONS

*The Actinomycetes*, vol. II, pp. 324–325, (1961).
*Bergy's Manual of Determinative Bacteriology*, 8th Edition, pp. 782–783 (1974).
*International Journal of Systematic Bacteriology*, vol. 22, pp. 265, 271 and 272 (1972).
*Applied Microbiology*, vol. 6, pp. 52–79 (1958).
*Method in Enzymology*, vol. XVIIB, pp. 306–317 (1971).
*Biochemical Pharmacology*, vol. 31, pp. 915–919 (1982).

Primary Examiner—Sidney Marantz
Assistant Examiner—K. S. Moss
Attorney, Agent, or Firm—Wenderoth, Lind & Ponack

[57] ABSTRACT

Novel peptide B-52653 having the formula:

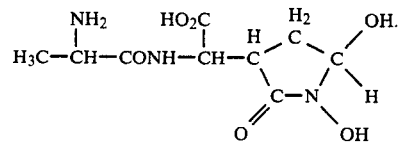

which is produced by cultivating a microorganism belonging to the genus Streptomyces and being capable of producing B-52653 in a culture medium, whereby B-52653 is elaborated and accumulated in the cultured broth and is recovered.

B-52653 is useful as a germicide or disinfectant, and a possibility of the present substance as an antifibrotic agent is suggested.

2 Claims, No Drawings

STREPTOMYCES ALBULUS SUBSP. OCHRAGERUS SUBSP. NOV. CULTURE FOR MAKING PEPTIDE

The present invention relates to a novel peptide B-52653 which is biologically active compound and a method of producing the same.

It is well known that soil microorganisms isolated from a soil sample produce various biologically active compounds including antibiotics. In search of new biologically active compounds, the present inventors collected a large number of soil samples, cultivated the microorganisms isolated from the samples and detected the cultures for inhibitory activity of cell wall synthesis and collagen-proline hydroxylase in culture broth. A new biologically active peptide was discovered in the culture broth of a microorganism. It was found that this compound not only inhibits growth of gram-positive and gram-negative bacteria through its cell wall synthesis inhibitory activity but also has collagen-proline hydroxidase inhibitory activity, that said microorganisms belong to the genus Streptomyces, that said peptide can be produced and accumulated in the culture broth by cultivating said microorganism in an appropriate culture medium under suitable cultural conditions. The present invention was accomplished based on the above-mentioned findings. The present inventors named the above new peptide B-52653. The above findings and subsequent studies have now resulted in the present invention.

The present invention is therefore directed to (1) a novel peptide B-52653, which has the formula:

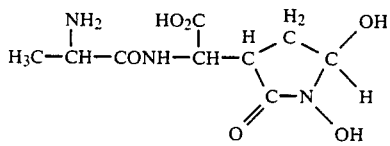

and (2) a method of producing said peptide, B-52653, characterized by cultivating a B-52653-producing strain of the genus Streptomyces to thereby cause the strain to elaborate and accumulate B-52653 in the culture broth and isolating the B-52653 from said broth.

The present invention is carried into practice using a microorganism of the genus Streptomyces that is able to elaborate the novel peptide B-52653. As an example of said B-52653-producing microorganisms, there may be mentioned Streptomyces sp. strain No. B-52653 which is a strain isolated from a soil sample obtained in Akashi City, Hyogo Prefecture, Japan, by the present inventors.

In this specification, the above-mentioned novel peptide B-52653 will sometimes be referred to briefly as B-52653, and said Streptomyces sp. strain No. B-52653 as strain No. B-52653.

(A) Microbiological characteristics of Strain No. B-52653

The microbiological characteristics of Strain No. B-52653 were investigated by the procedure of Schirling and Gottlieb [International Journal of Systematic Bacteriology 16, 313–340, 1966]. The following are the results of cultivation of the strain at 28° C. for 21 days.

(1) Morphological characteristics

Generally, on agar media, it gives a vegetative mycelium which is well branched and elongated, with its aerial mycelium being monopodially branched. Many of the spore chains form spiral or loop, and some are flexuous. In many instances, each spore chain is composed of more than 10 spores. The spores are oval or elliptical, ranging from 0.8 to 1.2 $\mu m \times 1.0$ to 1.5 $\mu m$ with spiny surface. Neither flaggella nor sporangia were observed.

(2) Cultural characteristics

The present strain grows well on various media, producing abundant spores, and the aerial mycelium is light gray to brownish gray. The reverse color ranges from pale yellow to brown, and on a few kinds of media, may produce light yellow to light brown soluble pigments.

(a)
 Sucrose nitrate agar
 Growth (G): moderate
 Aerial mycelium (AM): moderate, light brownish gray to Dusty Peach (5cb-5ec)*
 Soluble pigment (SP): none (b)
 Glucose asparagine agar
 (G): moderate
 (AM): abundant, Ashes (5fe)*
 (SP): none (c)
 Glycerin asparagine agar
 (G): moderate
 (AM): abundant, Silber Gray (3fe)*
 (SP): Lt Tan (3gc)*

(d)
 Starch agar
 (G): moderate
 (AM): abundant, Silver Gray (3fe)*
 (SP): none (e)
 Tyrosine agar
 (G): moderate
 (AM): moderate, Lt Ivory (2ca)* to Pussywillow Gray (5dc)*
 (SP): Rose Taupe (5ig)*

(f)
 Nutrient agar
 (G): moderate
 (AM): moderate, white to Pearl (3ba)*
 (SP): none (g)
 Yeast extract malt extract agar
 (G): abundant
 (AM): abundant, Beaver (4li)* to Lead Gray (5ih)*
 (SP): none, or pale yellow-brown (h)
 Oatmeal agar
 (G): abundant
 (AM): abundant, Silver Gray (3fe)*
 (SP): Honey Gold (2ic)*

(i)
 Calcium malate agar
 (G): moderate
 (AM): moderate, Bisque (3ec)*, to white
 (SP): Lt Fawn (4ge)*

*The color codes according to The Color Harmony Manual, the Fourth Edition, Container Corporation of America, 1958.

(3) Physiological characteristics (a) Temperature range for growth: 9°–40° C.
(b) Liquefaction of gelatin (glucose peptone gelatine): positive (weak)
(c) Hydrolysis of starch: positive
(d) Coagulation of skimmed milk: peptonized
(e) Production of melanoid pigments: Tyrosine agar: false positive Peptone yeast agar: negative (4) Assimilation of carbon sources

| L-arabinose | ± | D-xylose | ± |
| D-glucose | +++ | D-fructose | +++ |
| Sucrose | ++ | Inositol | +++ |
| L-rhamnose | + | Raffinose | ± |
| D-mannitol | +++ | Control | ± |

(Note)
+++: abundant growth
++: good growth
+: growth
±: slight growth

As to the above-mentioned characteristics of strain No. B-52653, reference was made to S. A. Waksman: The Actinomycetes, Vol. 2 (The Williams and Wilkins Co., 1961); R. E. Buchanan and N. E. Gibbons (ed.), Bergy's Manual of Determinative Bacteriology, 8th Edition, 1974; International Journal of Systematic Bacteriology Vol. 18, No. 2, pp. 69–189 and No. 4, pp. 279–392 (1968), ditto Vol. 19, No. 4, pp. 391–512 (1969) and ditto Vol. 22, No. 4, pp. 265–394 (1972), and other literature.

The taxonomic position of this strain based on the above-mentioned characteristics thereof is that it apparently belongs to the section Spirales or Retinacuriapelti and the Gray series as proposed by Pridham et al (Applied Microbiology 6, 52–79, 1958). As a known species which seems to be most closely related to the present strain, there may be mentioned *Streptomyces albulus*. Accordingly, a comparison was made of strain No. B-52653 with *Streptomyces albulus* IFO 13410 (ISP 5492). Strain No. B-52653 produces a light brown-gray aerial mycelium on sucrose nitrate agar and a light yellow-gray aerial mycelium on glucose nitrate agar. When grown on calcium malate agar, the same strain produces a light brown soluble pigment. Moreover, it grows utilizing L-rhamnose and sucrose. On the other hand, *Streptomyces albulus* produces a white aerial mycelium on sucrose nitrate agar and glucose nitrate agar and does not produce a soluble pigment on calcium malate agar. Moreover, the latter strain does not assimilate L-rhamnose or sucrose and, therefore, does not grow on these carbon sources.

The above results suggested that strain No. B-52653 was a novel subspecies of *Streptomyces albulus* and, accordingly, the strain was proposed the name *Streptomyces albulus* subsp. *ochragerus* subsp. nov.

This strain No. B-52653 has been deposited in Fermentation Research Institute, the Agency of Industrial Science and Technology (FERM), Ibaragi, Japan under the deposit number of FERM BP-273, Institute for Fermentation, Osaka (IFO), Japan under the accession number of IFO 14072, and The American Type Culture Collection (ATCC), U.S.A. under the accession number of ATCC 31713.

While, as mentioned above, strain No. B-52653 is a new strain of the genus Streptomyces, and it may undergo variation and mutation, as a general trait of microorganisms, either spontaneously or under the influence of mutagen. For example, mutants of the strain can be obtained by means of X-rays, gamma-rays, ultraviolet light or other radiation, monospore separation, treatment with various chemicals, cultivation on media containing such chemicals, and so forth. These mutants, as well as spontaneous mutants, can also be employed for the purposes of the present invention unless they are substantially considered to be new species in view of the above-mentioned or undermentioned microbiological characteristics and as long as they are capable of elaborating B-52653. By way of example, when strain No. B-52653 is subjected to various mutagenic treatments, there are obtained mutants which produce yellow or blue aerial mycelia.

The culture medium used for the cultivation of this invention may be either liquid or solid, only if it contains nutrients which the strain employed is capable of utilizing. However, when mass production is contemplated, a liquid medium is more advantageous. In the medium are incorporated the carbon and nitrogen sources which the strain can assimilate and digest, inorganic materials, and trace nutrients. The carbon sources may include, for example, glucose, lactose, sucrose, maltose, dextrin, starch, glycerin, mannitol, sorbitol, oils and fats (e.g. soybean oil, lard oil, chicken oil, etc.), and the nitrogen sources may include, among others, meat extract, yeast extract, dried yeast, soybean flour, corn starch liquor, peptone, cottonseed flour, spent molasses, urea, ammonium salts (e.g. ammonium sulfate, ammonium chloride, ammonium nitrate, ammonium acetate, etc.) and so on. In addition, there are incorporated suitable amounts of salts of sodium, potassium, calcium, magnesium, etc.; salts of iron, manganese, zinc, cobalt, nickel, etc., salts of phosphoric acid, boric acid, etc., and salts of organic acids such as acetic acid, propionic acid, etc. There may also be added amino acids (e.g. glutamic acid, aspartic acid, alanine, lysine, valine, methionine, proline, etc.), peptides (e.g. dipeptides, tripeptides, etc.), vitamins (e.g. $B_1$, $B_2$, nicotinic acid, $B_{12}$, C, etc.), nucleic acids and related compounds (e.g. purine or pyrimidine derivatives). Of course, for the purpose of adjusting the pH of the medium, inorganic or organic acids, alkalis, buffers, etc. may be added to the medium. Suitable amounts of oils, surfactants, etc. may also be added for defoaming purposes.

The cultivation may be carried out by stationary culture, shaking culture, submerged culture or other known cultural procedure. For mass fermentation, the procedure of so-called submerged culture is of course advantageous. While, of course, the cultural conditions depend on the condition and composition of medium, particular strain used, cultural method, etc., cultivation is usually conducted at a temperature of 20° to 35° C. and with an initial pH in the range of pH about 5 to 8. Preferred conditions are 23° to 32° C. and pH 5.5 to 7.0 (initial). While the cultivation time is also dependent on the above-mentioned conditions, cultivation is preferably continued until the amount of the present peptide produced reaches maximal. The time required for attaining such a concentration maximum is normally about 2 to 8 days in the case of shaking or aerated stirring culture using a liquid medium.

The pH suited to the production of the present peptide is weakly acidic, the optimum range being pH 5.5 to 7.0, and the output of the substance can be increased by controlling the pH of the medium with an acid or alkali. Thus, the yield of the substance can be considerably increased by adding inorganic phosphates in a concentration of 50 to 1000 ppm to the medium or by using saccharides such as glucose, starch or/and sucrose as carbon sources together with selected nitrogen sources and inorganic salts.

While its proportion varies with cultural conditions, B-52653 is usually accumulated extracellularly, with about 10% of the total yield being sometimes detected in the cells.

The present peptide thus produced in the culture broth can be assayed by the agar-well method or paper disk method using a drug-resistant mutant of *Staphylococcus aureus* as the test organism and B-52653 as the reference standard. Medium A [glucose 3%, sodium glutamate 0.5%, $K_2HPO_4$ 0.05%, $MgSO_4.7H_2O$ 0.05%, KCl 0.05%, yeast extract (Difco) 0.05%, Casamino acid (Difco) 0.02%, agar (Difco)].

The present peptide is mostly produced in the filtrate of the culture broth. The B-52653 thus produced can be isolated by the procedures conventionally used for harvesting microbial metabolites from culture broths, either as used singly or in a combination or as applied in repetition. Thus, for example, there may be employed such procedures as filtration, centrifugation, dialysis, concentration, drying, freeze-drying, adsorption and desorption, means utilizing a difference in solubility in different solvents (e.g. precipitation, crystallization, recrystallization, extraction counter-current distribution, etc.), chromatography, etc.

More particularly, since B-52653 is produced and accumulated extracellularly for the most part, this peptide is preferably recovered from the liquid fraction of the culture broth after removal of the cellular fraction. Moreover, because this peptide is an amphoteric water-soluble compound having carboxyl and amino functions, it can be advantageously isolated and purified from the liquid fraction of the broth by taking advantage of this property.

The chromatography referred to above may be advantageously conducted using cation and anion exchangers (e.g. ion exchange resins, Sephadex ion exchangers, ion exchange cellulose, etc.), gel permeation carriers [e.g. Sephadex (Pharmacia Fine Chemicals, Sweden), Biogel (Bio-Rad Laboratories, U.S.A.), preferably Sephadex LH-20 Pharmacia Fine Chemicals, Sweden], activated carbon, high-porous polymers [e.g. preferably Amberlite XAD-2 (Rohm and Haas Co., U.S.A.), Diaion HP-10 (Mitsubishi Kasei Kogyo, Japan)], alumina, florisil, silica gel, cellulose and so on.

The present invention isolated and purified the present compound by the above-mentioned procedures, investigated its physicochemical properties, and also through an independent research, found that it is a new compound of the following structural formula:

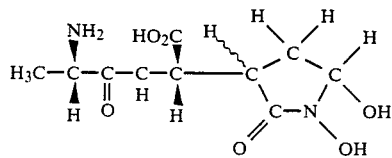

B-52653 can be produced in the above manner. Its physicochemical properties, as measured with the samples produced in accordance with Examples 1 and 2, are as follows.

(1) White powder (2) Elemental analysis: Calcd. for $C_9H_{15}N_3O_5.H_2O$: C, 38.43; H, 6.81; N, 14.94, Found: C, 38.44; H, 6.34; N, 14.78.

(3) Molecular weight (neutralization equivalent) and pKa'

The neutralization equivalent determined from the dissociation curve (titration in an aqueous solution containing 0.1N—HCl with 0.1N—NaOH) is 140±10, and the pH of the solution at the half-equivalent point determined from the dissociation curve is Ph 8.3±0.5. This dissociation curve is considered to be a composite of the dissociation curves of two dissociable groups having pKa' values close to each other (presumably at about 7.6 and about 8.8, although accurate pKa' values could not be measured because of the absence of an inflection point). Therefore, the molecular weight of the present peptide was assumed to be 280±20. When 1N—HCl was added to an aqueous solution of this substance and titration was performed with 1N—NaOH as aforesaid, a dissociable group having a pKa' value at about 3.15 was also detected.

(4) Optical rotation $[\alpha]_D^{25} + 50° \pm 5°$ (c=1.0, $H_2O$)

$[\alpha]_D^{25} + 62° \pm 5°$ (c=1.0, 0.1N HCl)

$[\alpha]_D^{25} + 50° \pm 5°$ (c=1.0, 0.1N NaOH)

(5) Ultraviolet absorption spectrum

The ultraviolet absorption spectrum of the present substance in aqueous solution shows no characteristic absorption maximum, except end absorptions, between 220 and 360 nm.

(6) Infrared absorption spectrum

The wave-numbers ($cm^{-1}$) of main absorption peaks in the infrared spectrum (KBr) are as follows. P 3400, 1690, 1610, 1395, 1265, 1205, 1080

(7) Nuclear magnetic resonance spectrum

The following nuclear magnetic resonance spectrum was observed in deuterium oxide using a Varian EM-390 (90 MHz) spectrometer.

δ: 1.70 (3H, d, J=7); 1.75 (m), 2.26 (m), 2.78 (m) (total 2H); 3.24 (1H, m), 4.26 (1H, q, J=7), 4.71 (1H, d, J=4.5), 5.38 (1H, m).

(8) Color reactions

Ninhydrin reaction: positive
Greig-Leaback peptide reaction: positive
Sakaguchi reaction: negative
Anthrone-sulfuric acid reaction: negative
Orcin-sulfuric acid reaction: negative (9) Solubility Readily soluble in water, but either only sparingly soluble or insoluble in organic solvents such as methanol, ethanol, acetone, chloroform, ethyl acetate, benzene, ethyl ether, petroleum ether, pyridine, glacial acetic acid, dimethylformamide, dimethyl sulfoxide, etc.

(10) Thin-layer chromatography (Merck's precoated TLC plate, silica gel 60F-254)

| Solvent systems | Rf |
| --- | --- |
| 1-Butanol-acetic acid-water (3:1:1) | 0.15 |
| 1-Butanol-pyridine-acetic acid-water (4:1:1:2) | 0.08 |
| 1-Propanol-water (7:3) | 0.13 |
| 2-Propanol-diisopropyl ether-60% formic acid (4:3:3) | 0.16 |
| Chloroform-methanol-17% aqueous ammonia (2:2:1) | 0.17 |

Antimicrobial activity

In the assays employing bacteria as test organisms, a loopful of $10^6$ CFU (cell forming unit)/ml was used as the inoculum and the MIC's were determined after incubation at 37° C. for 18–20 hours. In the case of fungi and yeasts, a loopful of each microorganism was milled thoroughly, a loopful of the resultant suspension was inoculated, and the MIC was determined after incubation at 28° C. for 2 or 3 days. The measurement of MIC was carried out by the agar dilution method using the media shown in the table.

It will be apparent from the table that B-52653 displays strong activity against gram-positive and gram-negative bacteria and that this substance is as active against various antibiotic-resistant microorganisms as against the corresponding susceptible strains. It has also been shown that the present substance displays strong activity against certain phytopathogenic bacteria.

| Test organism | Medium | MIC ($\mu$g/ml) |
| --- | --- | --- |
| Staphylococcus aureus IFO 13276 | I | 0.39 |
| Staphylococcus epidermidis FS 5010 | I | 0.39 |
| Bacillus subtilis PCI 219 | II | 6.25 |
| Bacillus cereus IFO 3001 | II | 3.13 |
| Bacillus megaterium IFO 3970 | II | 0.1 |
| Escherichia coli NIHJ JC-2 | II | 3.13 |
| Escherichia coli 0-111 | II | 6.25 |
| Escherichia coli K-12 W3110 | II | 3.13 |
| Escherichia coli TN 647 | II | 3.13 |
| Proteus vulgaris IFO 3988 | II | 1.50 |
| Proteus mirabilis IFO 3847 | II | 1.56 |
| Proteus morganii IFO 3168 | II | 3.13 |
| Klebsiella pneumoniae IFO 3512 | II | 12.5 |
| Klebsiella pneumoniae GN 3848 | II | 6.25 |
| Citrobacter freundii TN 457 | II | 1.56 |
| Citrobacter freundii TN 564 | II | 3.13 |
| Enterobacter cloacas IFO 12937 | II | 25 |
| Enterobacter aerogenes TN 582 | II | 6.25 |
| Salmonella typhimurium LT-2 | II | 0.78 |
| Salmonella enteritidis IFO 3313 | II | 0.2 |
| Serratia marcescens IFO 12648 | II | 0.78 |
| Serratia marcescens TN 24 | II | 0.2 |
| Pseudomonas aeruginosa IFO 3080 | II | >100 |
| Pseudomonas aeruginosa J-31 | II | >100 |
| Alternaria kikuchiana IFO 7515 | III | >100 |
| Pyricularia oryzae KHG-1 | III | 10 |
| Cochlioborus miyabeanus IFO 5277 | III | 100 |
| Botrytis cinerea TKF-12 | III | 50 |
| Sclerotinia sclerotiorum IFO 9395 | III | 1 |
| Pellicularis sasakii KHG-2 | III | 20 |
| Penicillium chrysogenum IFO 4626 | IV | >100 |
| Aspergillus niger IFO 4066 | IV | >100 |
| Saccharomyces cerevisiae IFO 0209 | IV | 12.5 |
| Candida albicans IFO 0538 | IV | >100 |

Medium I: 3% glucose, 0.5% sodium glutamate, 0.05% $K_2HPO_4$, 0.05% $MgSO_4.7H_2O$, 0.05% KCl, 0.05% yeast extract (Difco), 0.02% Casamino acid, 1.5% agar (pH 7.0).

Medium II: 0.5% glucose, 0.01% yeast extract, 0.1% $(NH_4)_2SO_4$, 0.01% $MgSO_4.7H_2O$, 0.05% sodium citrate, 0.2% $KH_2PO_4$, 0.7% $K_2HPO_4$, 1.5% agar (pH 7.0) [F. R. Atherton et al. Antimicrobial Agents and Chemotherapy 15, No. 5, 677–683 (1979)].

Medium III: potato sucrose agar

Medium IV: Peffer's modified agar medium: 3.0% sucrose, 0.2% L-asparagine, 0.3% $NH_4NO_3$, 0.1% $KH_2PO_4$, 0.1% $MgSO_4.7H_2O$, 0.001% Versenol*, agar 1.5% (pH 7.0) [* iron sodium ethanolethylene diaminetriacetate 50%].

The medium IV was supplemented with the following substances (per 100 ml) before use: 100 $\mu$g vitamin $B_1$ hydrochloride, 100 $\mu$g vitamin $B_2$, 100 $\mu$g calcium pantotheate, 100 $\mu$g nicotinic amide, 0.5 $\mu$g biotin, 50 $\mu$g folic acid, 200 $\mu$g vitamin $B_6$ hydrochloride, 50 $\mu$g p-aminobenzoic acid, 0.2 $\mu$g vitamin $B_{12}$.

Anti-infective effects in mice

Male mice of the ICR/SLC strain, 4 weeks of age, were intraperitoneally infected with $2 \times 10^8$ CFU cells from an overnight culture of Staphylococcus aureus E-97 in Brain heart infusion broth (Difco). Immediately thereafter, an aqueous solution of B-52653 was intraperitoneally administered in a single dose. As shown below, the above treatment had a prophylactic effect against infection.

| | Dosage (mg/kg) | | | | | | | |
| --- | --- | --- | --- | --- | --- | --- | --- | --- |
| | 3.13 | 6.25 | 12.5 | 25 | 50 | 100 | $ED_{50}$ | (mg/kg) |
| S/T | 1/5 | 2/5 | 2/5 | 3/5 | 3/5 | 5/5 | | 17.7 |

*S: the number of surviving animals
T: the number of mice submitted to the test

Collagen proline hydroxylase inhibitory activity

Organ fibrosis, inclusive of hepatic cirrhosis and pulmonary fibrosis, has been considered to be a disease caused by a pathological overgrowth of collagen, and an inhibitor of the above enzyme is thought to be of use for suppressing such fibrosis.

The collagen prolyl hydroxylase inhibitory activity of B-52653 was assayed by the method of R. E. Rhoads et al. [(Methods in Enzymology XVII B, 306 (1971)]. The assay revealed that this substance causes a 50% inhibition at the concentration of 270 $\mu$g/ml. Then, the collagen biosynthesis inhibitory action of B-52653 in rats was investigated by the B method of Ishimaru et al. (Ishimaru T., Kanamaru, T. and Okazaki, H., the Proceedings of the 1979 Congress of the Japanese Society of Agricultural Chemistry, p. 373). The results were that the collagen synthesis inhibition rates in rats given 50 mg/kg, 100 mg/kg and 200 mg/kg were 30%, 43% and 55%, respectively.

Thus, a possibility of the present invention substance as an antifibrotic agent is suggested.

Toxicity

In acute toxicity tests in which B-52653 was administered to mice by the intravenous and intraperitoneal routes, no death occurred even at the high dose of 1000 mg/kg, nor was observed any particular abnormality during a 7-day observation period following the administration or on autopsy. It is, therefore, considered that B-52653 is a very sparingly toxic substance.

As described above in detail, the present substances B-52653 has biological activities such as antimicrobial activity and activity to suppress fibrosis of animal tissues.

The present substance in the form of an aqueous solution from about 10 to about 100 μg/ml can be used as a disinfectant for bird cages, laboratory equipment, human hands, etc.

Because the present substance has activity to inhibit collagen prolyl hydroxylase activity, it is of value as a reagent for a study of the mechanism of collagen biosynthesis. It is also a promising application for the present substance to aseptically dissolve this substance in sterile physiological saline at the rate of about 2 to 10 g per 20 to 100 ml/day and administer the solution to humans by intravenous drip infusion for inhibition of the progress of hepatic fibrosis.

The following examples are further illustrative of this invention.

EXAMPLE 1

Strain No. B-52653 (IFO 14072, ATCC 31713) was inoculated on glucose asparagine agar and incubated at 24° C. for 10 days. The grown spores were scraped into sterile water to prepare a spore suspension (viable cells: $3 \times 10^8$/ml), which was stored in a refrigerator for use as an inoculum. One milliliter of the inoculum was inoculated a 2-liter Sakaguchi flask containing 500 ml of a sterilized preculture medium (35 g corn steep liquor, 10 g Proflo, 1 g K$_2$HPO$_4$, 15 g CaCO$_3$, 20 g glucose, 1 l tap water; pH 6.5), and the flask was incubated on a reciprocating shaker at 28° C. for 40 hours. A 500 ml portion of the resultant culture was transferred to a 200-liter stainless steel fermentor containing 100 l of a sterilized preculture medium similar to the above, and cultivation was carried out at 28° C. for 24 hours with aeration (50 l/min.) and stirring (200 r.p.m., ½ DT), and at an internal pressure of 1 kg/cm$^2$. The resulted seed culture (100 l) was further transferred to a 2000-liter stainless steel fermenter containing 900 l of a sterilized main fermentation medium consisting of 500 g DL-alanine, 1 kg DL-methionine, 1 kg FeSO$_4$, 500 g ZnSO$_4$, 200 g MgSO$_4$.7-H$_2$O, 100 g MnSO$_4$, 1.3 kg KH$_2$PO$_4$, 25 kg Proflo, 5 kg soybean flour, b 5 kg NH$_4$Cl, 12.5 kg CaCO$_3$ and 100 kg glucose [separately sterilized]). The fermentation was carried out at 28° C. for 54 hours with aeration (1000 l/min.) and stirring (200 r.p.m., ⅓ DT-2 stages), and at an internal pressure of 1 kg/cm$^2$. As a result, 254 μg/ml of B-52653 was produced in the broth.

EXAMPLE 2

To 980 l of the culture broth obtained in Example 1 was added 30 kg of Topcolite No. 34 (Toko Perlite Kogyo, Japan) as a filter aid, and the mixture was filtered by using a continuous vacuum filter. To 1350 l of the resulting filtrate was added 1.4 kg of oxalic acid and, after stirring for 30 minutes, 5 kg of Topcolite was added, followed by filtration. The resulting filtrate (1450 ml) was adsorbed on a column (350 l) of Amberlite 200 (H$^+$-form) and, after washing with water, elution was carried out with 0.5N-aqueous ammonia. The active fractions were collected and concentrated under reduced pressure. The concentrate (20 l) was adsorbed on a column (200 l) of activated carbon (Shirasagi for Chromatography, Takeda Chemical Industries, Ltd., Japan) and elution was carried out with water. The active fractions were combined and concentrated to 1.5 liters.

A 750 ml portion of the concentrate was adsorbed on a column (3 l) of alumina (Merck, West Germany activated alumina 90, neutral, activity I) and, after washing with water, elution was carried out with 0.2N-aqueous ammonia. The active fractions were collected and concentrated to dryness under reduced pressure. The residue (about 30 g) was dissolved in 60 ml of water, the solution was chromatographed on activated carbon (1 l), and elution was carried out with water. The active fractions were collected and concentrated under reduced pressure. The concentrate was further adsorbed on a column (700 ml) of Amberlite IRA 68 (Rohm and Haas Co. U.S.A.), and after washing with water and with 0.1M acetic acid, elution was carried out with 0.2M acetic acid. The active fractions were collected and concentrated under reduced pressure. The concentrate was adsorbed on a column (500 ml) of activated carbon and eluted with water. The active fractions were combined and concentrated under reduced pessure to give 3.9 g of white powder (purity: about 93%).

The above white powder (1.0 g) was dissolved in 4 ml of 50% aqueous methanol, diluted with 4 ml of 70% methanol and subjected to column chromatography on Sephadex LH-20 (Pharmacia Fine Chemicals, Sweden; swollen with 70% aqueous methanol). Elution was carried out with 70% aqueous methanol. The active fractions were pooled and the methanol was distilled off under reduced pressure. The resulting aqueous solution was freeze-dried to give 0.9 g of the desired B-52653.

What we claim is:

1. A biologically pure culture of the microorganism belonging to the genus Streptomyces having the characteristics identifiable with ATCC 31713, said culture being capable of producing in a culture medium containing assimilable carbon and digestible nitrogen sources, a recoverable amount of peptide B-52653 of the formula

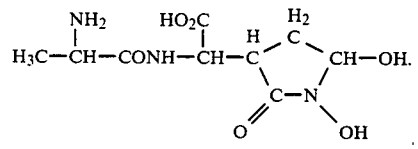

2. A method for producing peptide B-52653 of the formula

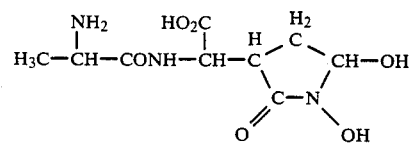

which comprises cultivating *Streptomyces albulus subsp. ochragerus subsp. nov.* (ATCC 31713) in a culture medium containing assimilable carbon sources and digestible nitrogen sources until peptide B-52653 is substantially accumulated in the culture broth, and isolating the same.

* * * * *